United States Patent
Lai et al.

(10) Patent No.: US 6,575,572 B2
(45) Date of Patent: Jun. 10, 2003

(54) METHOD AND APPARATUS FOR MEASURING OPTICAL ABERRATIONS OF AN EYE

(75) Inventors: Ming Lai, Dublin, CA (US); Jay Wei, Fremont, CA (US); Scott A. Meyer, Livermore, CA (US); James P. Foley, Fremont, CA (US); Jochen M. Horn, Pleasanton, CA (US)

(73) Assignee: Carl Zeiss Ophthalmic Systems, Inc., Dublin, CA (US)

( * ) Notice: Subject to any disclaimer, the term of this patent is extended or adjusted under 35 U.S.C. 154(b) by 92 days.

(21) Appl. No.: 09/960,113

(22) Filed: Sep. 21, 2001

(65) Prior Publication Data

US 2003/0058403 A1 Mar. 27, 2003

(51) Int. Cl.$^7$ .................................................. A61B 3/10
(52) U.S. Cl. ........................................................ 351/211
(58) Field of Search ............................ 351/211, 212, 351/216, 219, 221, 205, 206, 246

(56) References Cited

U.S. PATENT DOCUMENTS

| | | | |
|---|---|---|---|
| 5,629,765 A | 5/1997 | Schmutz | 356/121 |
| 5,777,719 A | 7/1998 | Williams et al. | 351/212 |
| 5,949,521 A | 9/1999 | Williams et al. | 351/246 |
| 6,000,800 A | 12/1999 | Webb et al. | 351/211 |
| 6,050,687 A | 4/2000 | Bille et al. | 351/212 |
| 6,086,204 A | 7/2000 | Magnante | 351/212 |
| 6,095,651 A | 8/2000 | Williams et al. | 351/246 |
| 6,199,986 B1 | 3/2001 | Williams et al. | 351/221 |
| 6,234,978 B1 | 5/2001 | Mihashi et al. | 600/558 |
| 6,264,328 B1 | 7/2001 | Williams et al. | 351/221 |
| 6,382,795 B1 * | 5/2002 | Lai | 351/212 |
| 6,439,720 B1 * | 8/2002 | Graves et al. | 351/211 |
| 6,497,483 B2 * | 12/2002 | Frey et al. | 351/212 |

FOREIGN PATENT DOCUMENTS

| | | | |
|---|---|---|---|
| WO | 27334 | 6/1999 | G01J/1/00 |
| WO | 10448 | 3/2000 | A61B/3/103 |

OTHER PUBLICATIONS

"Objective measurement of wave aberrations of the human eye with the use of a Hartmann–Shack wave–front sensor," J. Opt. Soc. Am. A, vol. 11, No. 7, pp. 1949–1957, Jul. 1994.
"Aberrations and retinal image quality of the normal human eye," J. Opt. Soc. Am. A, vol. 14, No. 11, pp. 2873–2883, Nov. 1997.
"Supernormal vision and high–resolution retinal imaging through adaptive optics," J. Opt. Soc. Am. A, vol. 14, No. 11, pp. 2883–2892, Nov. 1997.
"Optimal corneal ablation for eyes with arbitrary Hartmann-Shack aberrations," J. Opt. Soc. Am. A, vol. 15, No. 9, pp. 2580–2588, Sep. 1998.

* cited by examiner

Primary Examiner—George Manuel
(74) Attorney, Agent, or Firm—Michael B. Einschlag

(57) ABSTRACT

Embodiments of the present invention provide a method and apparatus for measurement of aberration of an eye. One or more embodiments provide an aberration measurement instrument that enables measurement wherein Hartmann-Shack spots have reduced speckle; one or more embodiments provide an aberration measurement instrument that enables measurement of an eye having a large diopter power variation over different zones of the eye; one or more embodiments provide an aberration measurement instrument that enables measurement with accommodation control; one or more embodiment provide an aberration measurement instrument wherein radiation reflected by a cornea and radiation scattered by intra-ocular elements are blocked; and one or more embodiment provide an aberration measurement instrument wherein a hazy background produced by radiation multiply scattered within an eye is reduced.

25 Claims, 8 Drawing Sheets

METHOD AND APPARATUS FOR MEASURING OPTICAL ABERRATIONS OF AN EYE

TECHNICAL FIELD OF THE INVENTION

The present invention pertains to method and apparatus for measuring aberrations of an imaging system such as an eye.

BACKGROUND OF THE INVENTION

A human eye is subject to a variety of optical aberrations. Accurate and complete measurement of such optical aberrations is essential for precise correction by customized photo-refractive surgery, by use of customized contact lenses, or by use of customized intra-ocular lenses.

Wavefront measurement is a commonly used method to determine optical aberrations of an eye. One prior art method of wavefront measurement utilizes a Hartmann-Shack sensor. In accordance with this method, a narrow beam of radiation output from a laser or a superluminescence diode is projected onto a retina of an eye through the optics of the eye. Then, radiation scattered from the retina passes through the optics, and emerges from the pupil (as is well known, the wavefront of the emerging beam carries information relating to aberration errors of the optics of the eye). Then, the wavefront of the emerging beam at the exit pupil plane of the eye is relayed (by relay optics) onto a Hartmann-Shack sensor, and output from the Hartmann-Shack sensor is used to measure the wavefront of the emerging beam. As is well known, for an emmetropic eye, i.e., an eye without aberration error, the wavefront of the emerging beam is a flat surface, whereas, for an eye that produces aberration errors, the wavefront of the emerging beam is distorted from the flat surface.

A Hartmann-Shack sensor typically comprises a lenslet array and a CCD camera, which CCD camera is typically located at a focal plane of the lenslet array. Whenever a beam to be measured is projected onto the Hartmann-Shack sensor, the lenslet array breaks the beam into sub-apertures, and forms a pattern of focal spots. The CCD camera records this pattern of focal spots, and a computer analyzes the pattern of focal spots to measure the wavefront of the beam.

Early uses of a Hartmann-Shack sensor in measuring aberration errors of an eye were disclosed by J. Liang et al. in an article entitled "Objective measurement of wave aberration of human eye with the use of Hartmann-Shack wave-front sensor," *J. Opt. Soc. Am. A*, Vol. 11, No. 7, July 1994, pp. 1949–1957; and by J. Liang et al. in an article entitled "Aberrations and retinal image quality of the normal human eye," *J. Opt. Soc. Am. A*, Vol. 14, No. 11, Nov. 1997, pp. 2873–2883. Further, D. R. Williams and J. Liang disclosed a configuration of an instrument using a Hartmann-Shack sensor in U.S. Pat. Nos. 5,777,719 and 5,949,521. Still further, J. Bille et al. disclosed an instrument using a Hartman-Shack sensor that is used to measure refractive properties of an eye in U.S. Pat. No. 6,050,687. Yet still further, D. R. Williams et al. disclosed an instrument using a Hartmann-Shack sensor for measurement of an eye's wave aberration in U.S. Pat. No. 6,199,986 ("the '986 patent").

Despite these prior art disclosures, several challenging issues remain involving instruments that use a Hartmann-Shack sensor. One challenging issue involving instruments that use a Hartmann-Shack sensor relates to reducing or minimizing speckle in Hartmann-Shack image spots. The speckle arises from the coherent nature of a probe beam combined with non-uniform scattering from the retina. The resulting speckle makes the Hartmann-Shack image spots irregular, and makes centroid detection of the spots less accurate. Although it is well known in the art that speckle can be reduced by using a probe beam having a short coherent length (for example, by using a probe beam produced using a superluminescence diode source), and by taking time averages over moving scatterers, such approaches have not been successful in removing speckle as an issue.

Another challenging issue involving instruments that use a Hartmann-Shack sensor relates to providing a measurement range that is large enough to account for defocusing error of a human eye. For example, defocusing error of a human eye typically ranges from −15D to +10D. Refractive surgery can usually correct defocusing error in a correction zone near a center of a pupil, for example, in a correction zone having a diameter of 3 to 6 mm. However, outside this correction zone, a post-operative eye has the same, or even a larger, defocusing error than that of the pre-operative eye. Therefore, an instrument that measures aberration errors of an eye, both inside and outside the correction zone, should have a diopter measurement range that is at least as large as one that refractive surgery can correct, i.e., a diopter measurement range of 10D or more. Further, this diopter measurement range should be achieved for any given measurement setting. One prior art approach used to resolve this issue entails using a set of compensation lenses to enlarge the measurement range of the instrument. However, this prior art approach cannot be used to measure an eye having a large defocusing error (as measured by diopter power variation) over different zones of the eye. Another prior art approach disclosed in the '986 patent entails adjusting a focal power of an optical relay stage. However, this prior art approach has the same limitation as the first one.

Another challenging issue involving instruments that use a Hartmann-Shack sensor relates to transferring a subject eye to a non-accommodative state, i.e., focusing the subject eye at a target an "infinite" distance away in a relaxed manner. This is particularly challenging whenever the subject eye has strong astigmatism. According to the '986 patent, a clinical study shows that accommodation effects aberration errors of the eye. As a result, preparing the subject eye in a controllable and reproducible manner is important in obtaining accurate and precise measurement of aberration errors.

Another challenging issue involving instruments that use a Hartmann-Shack sensor relates to reducing or minimizing: (a) reflection of a probe beam from a surface of a cornea and (b) scattering from intra-ocular elements of the eye. This reflection and scattering are problematic because they produce bright spots on a Hartmann-Shack image, and as a result, they degrade the quality of a wavefront measurement. One prior art approach to resolving this issue is disclosed by D. R. Williams et al. in U.S. Pat. No. 6,264,328. This prior art approach entails illuminating the probe beam off-axis to prevent reflected radiation from being detected by the Hartmann-Shack sensor. However, this prior art approach is problematic for two reasons. First, this prior art approach introduces tilt into the wavefront, and the tilt angle depends on defocusing errors of the eye. Second, this prior art approach does not reduce scattering from intra-ocular elements.

Another challenging issue involving instruments that use a Hartmann-Shack sensor relates to reducing or minimizing the effect of multiply scattered radiation from interior portions of the eye. Such multiply scattered radiation appears as trace light that emerges from the pupil, and travels in all directions. This is problematic because such trace light produces a hazy background around Hartmann-Shack spots that degrades the quality of a Hartmann-Shack image.

In light of the above, there is a need in the art for method and apparatus for resolving one or more of the above-described issues.

SUMMARY OF THE INVENTION

One or more embodiments of the present invention advantageously satisfy the above-identified need in the art. For example, one or more embodiments of the present invention provide an aberration measurement instrument that enables measurement wherein Hartmann-Shack spots have reduced speckle. Specifically, one embodiment of the present invention is an aberration measurement instrument that comprises: (a) a probe beam projector that outputs a probe beam of radiation; (b) a coupler that couples the probe beam of radiation into the eye; (c) relay optics that relays a wavefront of an emerging beam at a pupil plane to a plane; (d) a Hartmann-Shack sensor disposed at the plane that produces a Hartmann-Shack spot pattern; and (e) a detector responsive to the Hartmann-Shack spot pattern; wherein the probe beam projector includes an oscillating lens.

One or more embodiments of the present invention provide an aberration measurement instrument that enables measurement of an eye having a large diopter power variation over different zones of the eye. Specifically, one embodiment of the present invention is an aberration measurement instrument that comprises: (a) a probe beam projector that outputs a probe beam of radiation; (b) a coupler that couples the probe beam of radiation into the eye; (c) relay optics that relays a wavefront of an emerging beam at a pupil plane to a plane; (d) a Hartmann-Shack sensor disposed at the plane that produces a Hartmann-Shack spot pattern; and (e) a detector responsive to the Hartmann-Shack spot pattern; wherein the relay optics has a magnification greater than 1.

One or more embodiments of the present invention provide an aberration measurement instrument that enables measurement with accommodation control. Specifically, one embodiment of the present invention is an aberration measurement instrument that comprises: (a) a probe beam projector that outputs a probe beam of radiation; (b) a coupler that couples the probe beam of radiation into the eye; (c) relay optics that relays a wavefront of an emerging beam at a pupil plane to a plane; (d) a Hartmann-Shack sensor disposed at the plane that produces a Hartmann-Shack spot pattern; and (e) a detector responsive to the Hartmann-Shack spot pattern; wherein the aberration measurement instrument further includes an optometer module coupled to the eye.

One or more embodiments of the present invention provide an aberration measurement instrument wherein radiation reflected by a cornea and radiation scattered by intraocular elements are blocked. Specifically, one embodiment of the present invention is an aberration measurement instrument that comprises: (a) a probe beam projector that outputs a probe beam of radiation; (b) a coupler that couples the probe beam of radiation into the eye; (c) relay optics that relays a wavefront of an emerging beam at a pupil plane to a plane; (d) a Hartmann-Shack sensor disposed at the plane that produces a Hartmann-Shack spot pattern; and (e) a detector responsive to the Hartmann-Shack spot pattern; wherein the aberration measurement instrument further includes an obscuration member located at or near a plane conjugate to the pupil plane.

One or more embodiments of the present invention provide an aberration measurement instrument wherein a hazy background produced by radiation that is multiply scattered within an eye is reduced. Specifically, one embodiment of the present invention is an aberration measurement instrument that comprises: (a) a probe beam projector that outputs a probe beam of radiation; (b) a coupler that couples the probe beam of radiation into the eye; (c) relay optics that relays a wavefront of an emerging beam at a pupil plane to a plane; (d) a Hartmann-Shack sensor disposed at the plane that produces a Hartmann-Shack spot pattern; and (e) a detector responsive to the Hartmann-Shack spot pattern; wherein the relay optics includes a dynamic haze stop located at approximately a conjugate plane of a retina.

DETAILED DESCRIPTION

Figure 1:
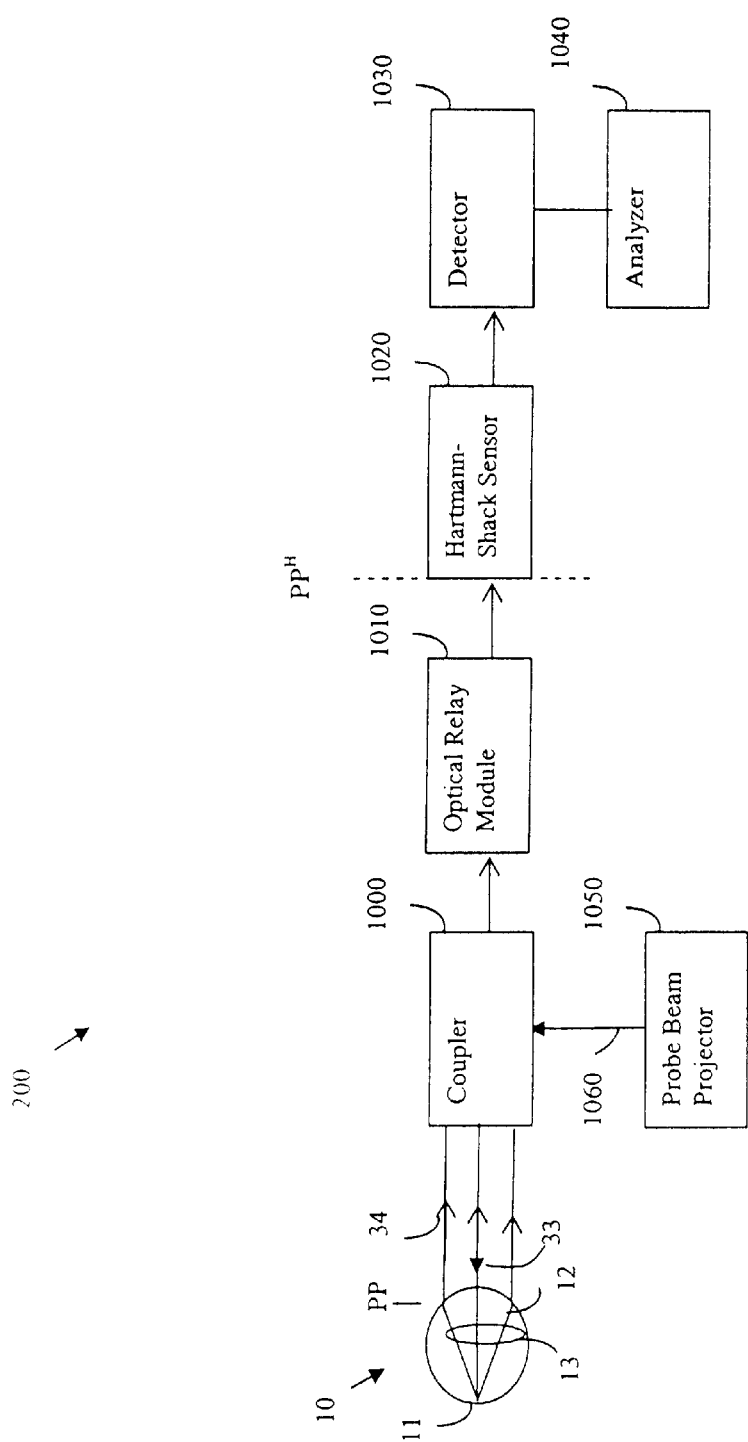
FIG. 1 is a schematic diagram of an aberration measurement instrument that is fabricated in accordance one embodiment of the present invention.

FIG. 1 is a schematic diagram of aberration measurement instrument 200 that is fabricated in accordance with the present invention. As shown in FIG. 1, probe beam projector 1050 outputs probe beam 1060 that impinges upon coupler 1000. Probe beam 1060 typically comprises radiation that is not detected by a patient such as, for example and without limitation, infrared or near infrared radiation. Thus, one can utilize a superluminescence diode having output in the near infrared spectrum range as a source of radiation for probe beam projector 1050. However, other radiation sources may also be used such as, for example and without limitation, a laser or a light emitting diode. Probe beam 33 output from coupler 1000 is directed through the optics of eye 10, including the cornea and crystalline lens 13, onto retina 11 of eye 10. Retina 11 scatters incident radiation from probe beam 33. The radiation scattered by retina 11 passes through the optics of eye 10, including crystalline lens 13 and the cornea, and emerges from eye 10 at exit pupil plane PP as emerging beam 34. As is well known, the wavefront of emerging beam 34 at exit pupil plane PP of eye 10 carries aberration information relating to the optical quality of the optics of eye 10. For example, for a perfect emmetropic eye without aberration error, the wavefront of emerging beam 34 at exit pupil plane PP is a flat plane. For a myopic or hyperopic eye, however, the wavefront of emerging beam 34 at exit pupil plane PP has the shape of a spherical surface. For an eye with high order aberrations, the wavefront of emerging beam 34 at exit pupil plane PP is distorted irregularly. Aberration measurement instrument 200 measures the wavefront profile of emerging beam 34 at exit pupil plane PP to determine aberration or refractive errors of the optics of eye 10.

The wavefront of emerging beam 34 at exit pupil plane PP passes through coupler 1000, and is relayed by optical relay module 1010. In one embodiment of the present invention, coupler 1000 comprises a polarizing beamsplitter. In such an embodiment, the polarizing beamsplitter reflects probe beam 1060, which is substantially linearly polarized, into probe beam 33 that impinges upon eye 10. Such a polarizing beamsplitter can be fabricated in accordance with any one of a number of methods that are well known to those of ordinary skill in the art and such polarizing beamsplitters are commercially available. Scattering depolarizes emerging beam 34. Thus, since emerging beam 34 passes through coupler 1000, when coupler 1000 comprises a polarizing beamsplitter, only a portion of depolarized, emerging beam 34 is passed to optical relay module 1010 (i.e., advantageously, the polarizing beamsplitter rejects reflections of initial polarization from, among other things, crystalline lens 13, the cornea, and retina 11). Optical relay module 1010 relays the wavefront of emerging beam 34 from exit pupil plane PP of eye 10 to conjugate plane $PP^H$ at Hartman-Shack sensor 1020. In particular, Hartman-Shack sensor 1020 comprises a lenslet array that is disposed at conjugate plane $PP^H$, which conjugate plane $PP^H$ is conjugate to exit pupil plane PP. As is well known, the lenslet array breaks the beam of scattered radiation into lenslet sub-apertures, and forms a Hartmann-Shack spot pattern at a focal plane of the lenslet array. A suitable lenslet array for use in the present instrument is commercially available from, for example, Adaptive Optics Associates of Cambridge, Mass. As is well known, the Hartmann-Shack spot pattern carries aberration information of the wavefront of emerging beam 34.

Next, as shown in FIG. 1, detector 1030 detects the Hartmann-Shack spot pattern. For example, in one embodiment, detector 1030 is a CCD camera that records the Hartmann-Shack spot pattern, and outputs a digital signal that is applied as input to analyzer 1040. In one embodiment, analyzer 1040 is embodied as a computer, for example, a personal computer. In accordance with one embodiment of the present invention, analyzer 1040 determines coordinates (for example, an x, y, z position) of a centroid of a plurality of the focal spots in accordance with any one of a number of methods that are well known to those of ordinary skill in the art. Next, analyzer 1040 determines a slope of each beam segment using the coordinates of the centroids to determine the slope of a portion of the beam that passes through a plurality of the elements of the lenslet array. Next, analyzer 1040 uses any one of a number of methods that are well known to those of ordinary skill in the art that uses the slopes of the beam segments to reconstruct the wavefront of beam 33 at plane $pp^H$. For example, in one such embodiment, analyzer 1040 fits the slopes of the beam segments to a set of Zernike polynomials to reconstruct the wavefront of beam 33 at plane $pp^H$ in accordance with a teaching of an article entitled "Objective measurement of wave aberrations of the human eye with the use of a Hartmann-Shack wave-front sensor" by J. Liang et al., *J. Opt. Soc. Am. A*, Vol. 11, No. 7, July 1994, pp. 1949–1957, and an article entitled "Aberrations and retinal image quality of the normal human eye" by J. Liang et al., *J. Opt. Soc. Am. A*, Vol. 14, No. 11, November 1997, pp. 2873–2883 (the "Liang articles"), which Liang articles are incorporated by reference herein. The wavefront of emerging beam 34 is then reconstructed at exit pupil plane P using a scale factor that is determined by optics relay module in accordance with any one of a number of methods that are well known to those of ordinary skill in the art. A review of the Hartmann-Shack wavefront sensor, and wavefront reconstruction is found in U.S. Pat. No. 5,777,719. Finally, the aberrations, i.e., refractive errors, of eye 10 are calculated by analyzer 1040 in accordance with any one of a number of methods that are well known to those of ordinary skill in the art using the reconstructed wavefront. For example, one such method is disclosed in a publication of R. W. Frey et al. on Jun. 3, 1999, WO 99/27334 entitled "Objective Measurement and Correction of Optical Systems Using Wavefront Analysis" wherein distortions of the wavefront are taken as an estimate of the aberrations, which publication is incorporated by reference herein (see also the Liang articles). An algorithm to do this, for use in analyzer 1040, for example, a computer algorithm, is commercially available from, for example, Adaptive Optics Associates of Cambridge, Mass.

I. Speckle Reduction

Figure 2:
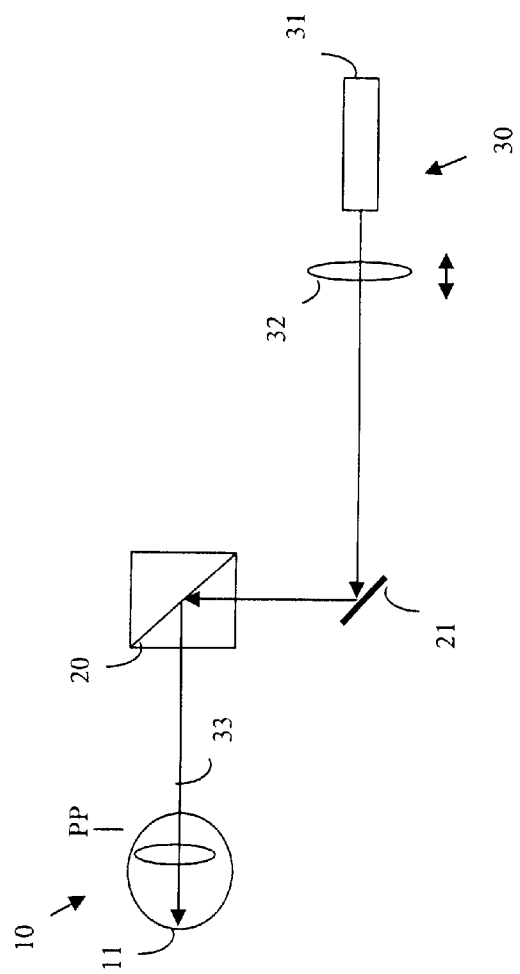
FIG. 2 is a schematic diagram of a probe beam projector with an oscillating lens that is used to fabricate an aberration measurement instrument in accordance with one or more embodiments of the present invention.

FIG. 2 is a schematic diagram of probe beam projector 30 that is used to fabricate an aberration measurement instrument in accordance with one or more embodiments of the present system. As shown in FIG. 2, radiation source 31 outputs a probe beam of radiation that is focused by lens system 32 (although lens system 32 is shown as being comprised of one lens, those of ordinary skill in the art will readily understand that lens system 32 may comprise one or more lenses). After being redirected by turning mirror 21, the probe beam of radiation impinges upon coupler 20. As those of ordinary skill in the art will readily appreciate, turning mirror 21 is used as a convenience to make the instrument more compact, but it is not necessary for operation. Turning mirror 21 can be fabricated in accordance with any one of a number of methods that are well known to those of ordinary skill in the art. Further, in one embodiment, coupler 20 is embodied as a polarizing beamsplitter. Radiation output from coupler 20 is applied as probe beam 33 to eye 10.

Advantageously, in accordance with these embodiments of the present invention, whenever lens system 32 comprises a lens system that is oscillated by a moving mechanism (not shown), speckle in resulting Hartmann-Shack images is reduced. The moving mechanism may be fabricated in accordance with any one of a number of methods that are well known to those of ordinary skill in the art such as, for example and without limitation, the use of a voice coil. In addition, the moving mechanism may operate in response to signals from, for example and without limitation, analyzer 1040 in accordance with any one of a number of methods that are well known to those of ordinary skill in the art. Further, whenever oscillating lens system 32 is used in conjunction with a low coherence radiation source 31, such as, for example and without limitation, a superluminescence diode, speckle in resulting Hartmann-Shack images is minimized. As a result, the precision of wavefront measurement, and consequent aberration measurement, is improved.

When lens system 32 shown in FIG. 2 is situated at a predetermined position along its optical axis, probe beam 33 impinges upon retina 11 in a spot having a predetermined spot size (as those of ordinary skill in the art will readily appreciate, which predetermined spot size is determined, among other things, by lens system 32 and the optics of eye 10). In accordance with one embodiment of the present invention, radiation output from source 31 is aligned to propagate in a direction that is substantially collinear with an optical axis of oscillating lens system 32, and to pass substantially through a center of lens system 32. As a result, probe beam 33 will travel in a direction that remains substantially stationary as lens system 32 oscillates about the predetermined position along the optical axis. Then, as lens system 32 oscillates rapidly along the optical axis about the predetermined position, the size of the spot in which probe beam 33 impinges on retina 11 will oscillate rapidly in a predetermined range (for example, for a substantially circular spot, the size of the spot will oscillate rapidly within a circular area defined by a predetermined diameter) while a centroid of the spot will remain substantially constant. Further, as the size of the spot on retina 11 varies, the relative phase of probe beam 33 will change at any two points across the spot. Therefore, the relative phase of radiation scattered by retina 11 will change rapidly (i.e., the spatial coherence of radiation scattered by retina 11 will be randomized), and as a result, speckle in the Hartmann-Shack spots will be reduced.

Lasers and superluminescence diodes are typical sources used to fabricate an aberration measurement instrument using a Hartmann-Shack sensor because of brightness and beam quality requirements. However, it is well known in the art that speckle occurs whenever a coherent beam, for example, a beam produced by a laser, is scattered by non-uniform scatterers. Because of this, if a laser were used to produce a probe beam in such an instrument, speckle in the Hartmann-Shack spots would be substantial, and accurate measurement thereof would be difficult. It is also well known in the art that a low coherence beam, such as one emitted from a superluminescence diode, produces less speckle than that produced by a laser beam. However, speckle produced using a beam produced by a superluminescence diode is still considerable because, even though its spatial coherence along the beam is much poorer than that of a laser beam, a beam produced by a superluminescence diode has good spatial coherence across the beam. Thus, in accordance with a further embodiment of the present invention, the speckle of Hartmann-Shack spots can be minimized by an embodiment that includes oscillating lens system 32 and probe beam source 31 wherein probe beam source 31 comprises a bright light source having poor temporal coherence such as, for example and without limitation, a superluminescence diode.

In one example of such an embodiment, the superluminescence diode has a wavelength centered at about 820 nm, and has a spectral bandwidth of about 25 nm. Further, the power of probe beam 33 that is projected into eye 10 is in a range of about 50 to about 100 microwatts. Still further, a diameter of the spot on retina 11 oscillates in a range of about 100 to about 200 micrometers. Still further, lens system 32 is a lens that has a focal length of about 10 mm, and that is oscillated over a linear distance of about 0.5 mm. Still further, a voice coil can be used as a moving mechanism in accordance with any one of a number of methods that are well known to those of ordinary skill in the art to oscillate lens system 32 at a resonant frequency of about 20 to about 100 Hz.

II. Enlarged Measurement Range

Figure 3:
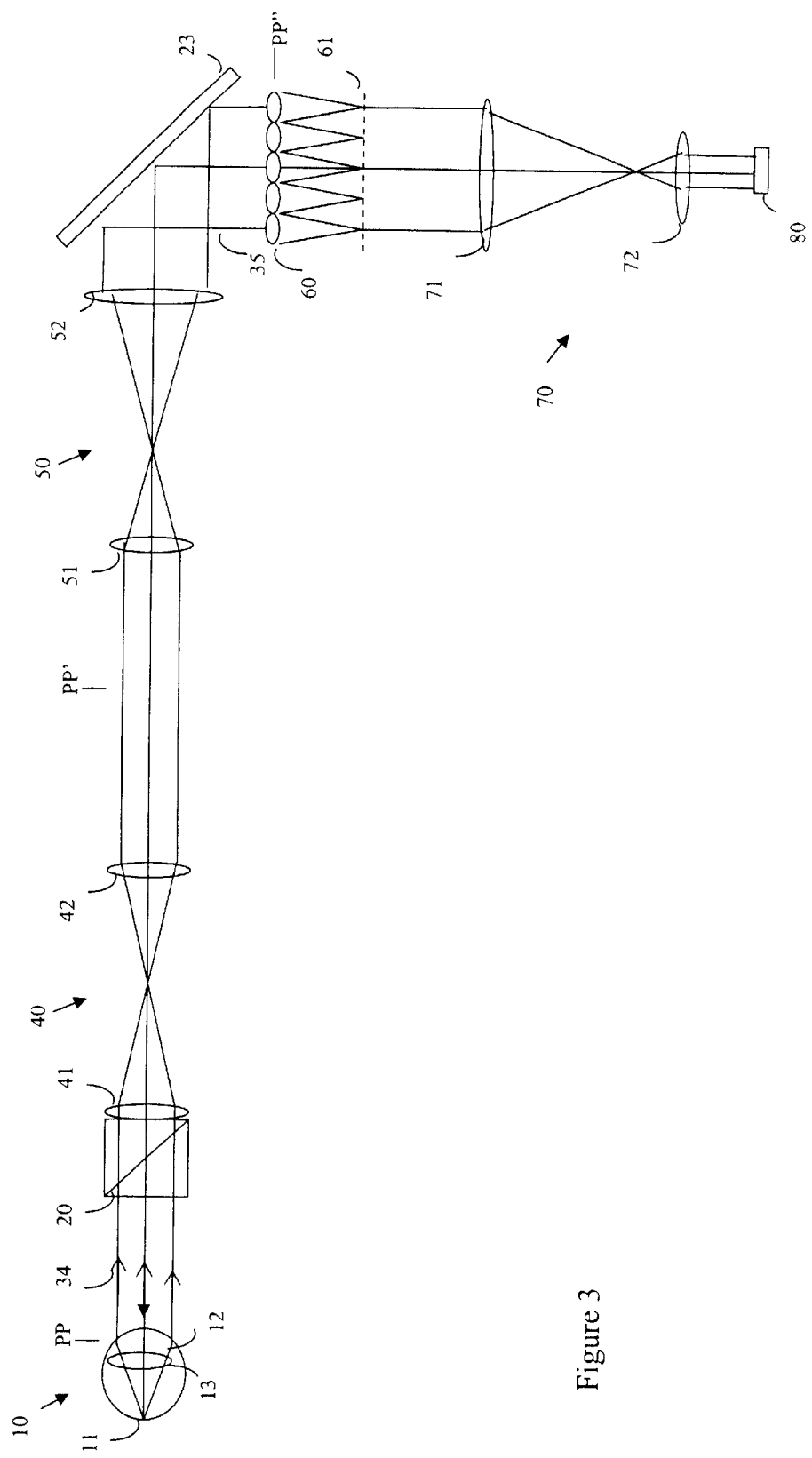
FIG. 3 is a schematic diagram of an optical configuration that is used to fabricate an aberration measurement instrument in accordance with one or more embodiments of the present invention.

FIG. 3 is a schematic diagram of an optical configuration that is used to fabricate an aberration measurement instrument in accordance with one or more embodiments of the present invention, which embodiments have an enlarged measurement range. That is, FIG. 3 shows an embodiment having an optical configuration that enables measurement of an eye having a large diopter power variation over different zones of the eye. The optical configuration shown in FIG. 3 is obtained from the optical configuration shown in FIG. 1 by embodying optical relay module 1010 of FIG. 1 so that it comprises first optical relay module 40 and second optical relay module 50, and by inserting optional optical image module 70 between Hartmann-Shack sensor 1020 and detector 1030. As shown in FIG. 3, first optical relay module 40 comprises lens systems 41 and 42 (although lens systems 41 and 42 are each shown as being comprised of one lens, those of ordinary skill in the art will readily understand that lens systems 41 and 42 may each comprise one or more lenses)—first optical relay module 40 may be fabricated in accordance with any one of a number of methods that are well known to those of ordinary skill in the art. Optical relay module 40 relays the wavefront of emerging beam 34 from exit pupil plane PP of eye 10 to first conjugate plane PP'. The wavefront is then relayed by second optical relay module 50 to impinge upon turning mirror 23, and from there, onto lenslet array 60. As shown in FIG. 3, second optical relay module 50 comprises lens systems 51 and 52 (although lens systems 51 and 52 are each shown as being comprised of one lens, those of ordinary skill in the art will readily understand that lens systems 51 and 52 may each comprise one or more lenses)—second optical relay module 50 may be fabricated in accordance with any one of a number of methods that are well known to those of ordinary skill in the art. As those of ordinary skill in the art will readily appreciate, turning mirror 23 is used as a convenience to make the instrument more compact, but it is not necessary for operation. Turning mirror 23 can be fabricated in accordance with any one of a number of methods that are well known to those of ordinary skill in the art. Lenslet array 60 (one embodiment of Hartmann-Shack sensor 1020 of FIG. 1) is disposed at second conjugate plane PP", which second conjugate plane PP" is conjugate to first conjugate plane PP' and to exit pupil plane PP. As shown in FIG. 3, optional optical image module 70 relays and focuses Hartmann-Shack spot pattern 61 that is formed at a focal plane of lenslet array 60 onto a sensing surface of CCD camera 80 (one embodiment of detector 1030 of FIG. 1). As shown in FIG. 3, optional optical image module 70 comprises lens systems 71 and 72 (although lens systems 71 and 72 are each shown as being comprised of one lens, those of ordinary skill in the art will readily understand that lens systems 71 and 72 may each comprise one or more lenses)—optical image module 70 may be fabricated in accordance with any one of a number of methods that are well known to those of ordinary skill in the art.

In accordance with this embodiment, first optical relay module 40 and second optical relay module 50, when taken together, have a magnification greater than one (1). Due to this magnification, the aperture (i.e., the pupil size) of the wavefront of emerging beam 34 at lenslet 60 is enlarged, but the diopter power of the wavefront of emerging beam 34 at lenslet array 60 is reduced. Then, in accordance with this embodiment, optical image module 70 has a magnification less than one (1), and it transfers Hartmann-Shack spot pattern 61 at the lenslet array focal plane to CCD camera 80. By utilizing the magnification and demagnification described above, an aberration measurement instrument can have a larger dioptric measurement range for a large pupil, while using a conventional CCD camera having a chip of limited sensing area.

In accordance with one such embodiment of the present invention, first optical relay module 40 comprises two substantially identical lens systems 41 and 42 that are installed in a confocal configuration to form a unit relay. Further in accordance with this one such embodiment, second optical relay module 50 comprises two lens systems 51 and 52 having different focal lengths to form a relay having a magnification M that is greater than one. As a result of the above, the wavefront at first conjugate plane PP' is the same as that at exit pupil plane PP, however, the wavefront at second conjugate plane PP" has an aperture that is M times larger, and a slope variation that is $M^2$ smaller than those of the wavefront at exit pupil plane PP. Thus, since lenslet array 60 (disposed at second conjugate plane PP") receives measurement beam 35 having a diameter that is M times as big as that of emerging beam 34, Hartmann-Shack spot pattern 61 at the lenslet focal plane is enlarged over one that would have resulted without the use of second optical relay module 50. Although the embodiment shown in FIG. 3 showed the use of two optical relay module having a magnification, when taken together, that is <1, embodiments of the present invention are not thusly limited. Thus, embodiments of the present invention can be fabricated using a single optical relay module having magnification M<1.

If Hartmann-Shack spot pattern 61 shown in FIG. 3 is larger than a sensing area of an available CCD camera, optional optical image module 70 may be used to reduce the size of Hartmann-Shack spot pattern 61 to fit onto the sensing area of CCD camera 80. For example, to do this, optical image module 70 may comprise lens systems 71 and 72 having different focal lengths to form a demagnification stage having a demagnification M'. In addition, one design of optical image module 70 ought to minimize field distortion from the lenslet focal plane to the sensor surface of CCD camera 80.

In one example of such an embodiment, the magnification of first optical relay module 40 is 1, the magnification M of second optical relay module 50 is 1.4, and the demagnification M' of optical image module 70 is 0.3. Using these modules, the measurement range of an aberration measurement instrument may be enlarged by a factor of 2 (i.e., $1.4^2$), while a ½" CCD camera chip having a sensing area of 6.4×4.8 mm can be used in CCD camera 80 to receive emerging beam 34 from an eye with pupil size of 8 mm. Further, lenslet array 60 has a sub-aperture of approximately 1 mm and a focal length in the order of magnitude of 10 mm. Such a lenslet array is commercially available from, for instance, Adaptive Optics Associate of Cambridge, Mass.

III. Optometer Integration

Figure 4:
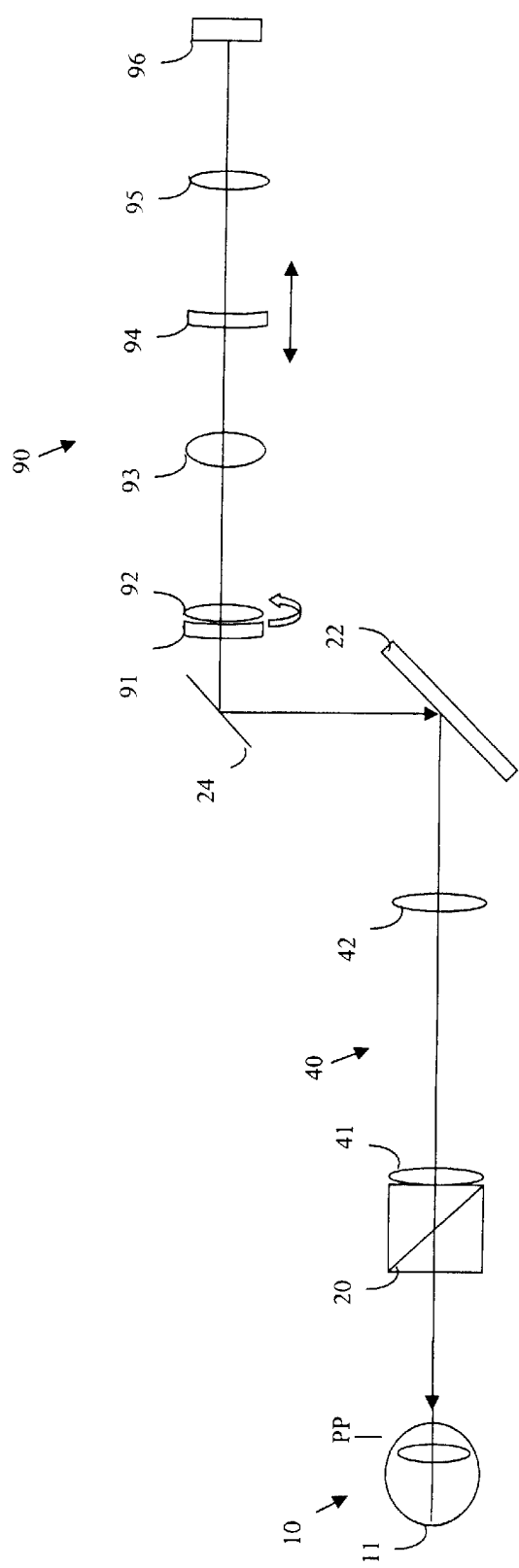
FIG. 4 is a schematic diagram showing an optometer module that is used to fabricate a wavefront instrument in accordance with one or more embodiments of the present invention.

FIG. 4 is a schematic diagram showing optometer module 90 that is used to fabricate an aberration measurement instrument in accordance with one or more embodiments of the present invention to provide accommodation control. In accordance with these embodiments, optometer module 90 compensates optically for defocusing error and astigmatism of eye 10, and leads eye 10 to focus onto a target appearing at a far distance ("infinity"). As shown in FIG. 4, optometer module 90 comprises first Stokes' lens system 91, second Stokes' lens system 92, first focal lens system 93, movable lens system 94, second focal lens system 95, and fixation target 96 (although first Stokes' lens system 91, second Stokes' lens system 92, first focal lens system 93, movable lens system 94, and second focal lens system 95 are each shown as being comprised of one lens, those of ordinary skill in the art will readily understand that lens systems 91–95 may each comprise one or more lenses). Many methods are well known to those of ordinary skill in the art for fabricating optometer module 90. Fixation target 96 is fabricated in accordance with any one of a number of methods that are well known to those of ordinary skill in the art, and fixation target 96 is illuminated by a white light source (not shown). As shown in FIG. 4, fixation target 96 is imaged into eye 10 through optical relay module 1010 of FIG. 1 (as shown in FIG. 4, optical relay module 1010 of FIG. 1 is embodied as optical relay module 40), and optometer lens systems 91–95. As shown in FIG. 4, radiation output from optometer module 90 is coupled into the aberration measurement instrument using beamsplitter 22. Beamsplitter 22 is designed, in accordance with any one of a number of methods that are well known to those of ordinary skill in the art, to transmit radiation in emerging beam 34 (for example, radiation emitted by source 31 of FIG. 2), and to reflect radiation generated in optometer module 90 (for example, white light). Although FIG. 4 shows that radiation output from optometer module 90 is coupled into the aberration measurement instrument after optical relay module 40, those of ordinary skill in the art will readily appreciate that embodiments of the present invention are not limited thereto. In particular, embodiments exist wherein radiation output from optometer module 90 may be coupled into the aberration measurement instrument a different positions. For example, radiation output from optometer 90 can be coupled before or after coupler 1000 shown in FIG. 1.

A position of movable lens system 94 along its optical axis can be changed in accordance with any one of a number of methods that are well known to those of ordinary skill in the art in response toga signal from, for example, analyzer 1040 of FIG. 1 to compensate for defocusing error of eye 10. For example, movable lens system 94 may be mounted on a moving mechanism such as a translation stage driven by a motor. Further, Stokes' lens systems 91 and 92 can be rotated independently electronically in accordance with any one of a number of methods that are well known to those of ordinary skill in the art in response to a signal from, for example, 1040 of FIG. 1, analyzer 1040 of FIG. 1 to compensate for astigmatism of eye 10. For example, Stokes' lens systems 91 and 92 may be mounted on a rotation stage driven, for example, by a motor. In one embodiment, first and second Stokes' lens systems 91 and 95 are cylindrical lenses.

In operation, a patient is asked to fixate on fixation target 96. The aberration measurement instrument then makes an initial measurement, and calculates an initial estimate of defocusing error and astigmatism of eye 10. In response, analyzer 1040 may drive an initial setting of optometer module 90 to compensate for the measured defocusing error and astigmatism to enable eye 10 to focus more clearly at a distant target (i.e., when looking through a properly accommodated optometer module 90, eye 10 will see a sharp fixation target 96 appearing at a far distance). For example, in one embodiment, analyzer 1040 sends a signal to a moving mechanism (not shown) for movable lens system 94 that causes to move movable lens system 94 to compensate for defocusing error of eye 10, and analyzer 1040 sends another signal to a rotating mechanism (not shown) for Stokes' lens systems 91 and 92 to cause it to rotate Stokes' lens systems 91 and 92 to compensate for astigmatism of eye 10. This step may be performed a number of times until the measured defocusing error and astigmatism of eye 10 are stabilized within a predetermined range. At this juncture, accommodation of eye 10 should be stabilized, and eye 10 will see fixation target 96 as a sharp image appearing at a far distance. A technique named fogging can also be implemented to further stabilize accommodation of eye 10. Fogging is a technique wherein a small, but extra amount of defocusing power (~0.5 diopter) is added into the optical path to lead the subject eye to focus slightly "beyond" infinity, which fogging technique is well known to those of ordinary skill in the art. In further embodiments, the adjustments of movable lens system 94 and Stokes' lens systems 91 and 92 can be done by an operator.

Lastly, a step of measuring eye 10 using the aberration measurement instrument is performed to determine optical aberrations of eye 10.

In one example of such an embodiment, movable lens system 94 can be adjusted to accommodate defocusing error from −15 diopters to +15 diopters. Further, Stokes' lens systems 91 and 92 can be adjusted to accommodate astigmatism up to 6 diopters at any orientation.

Figure 5:
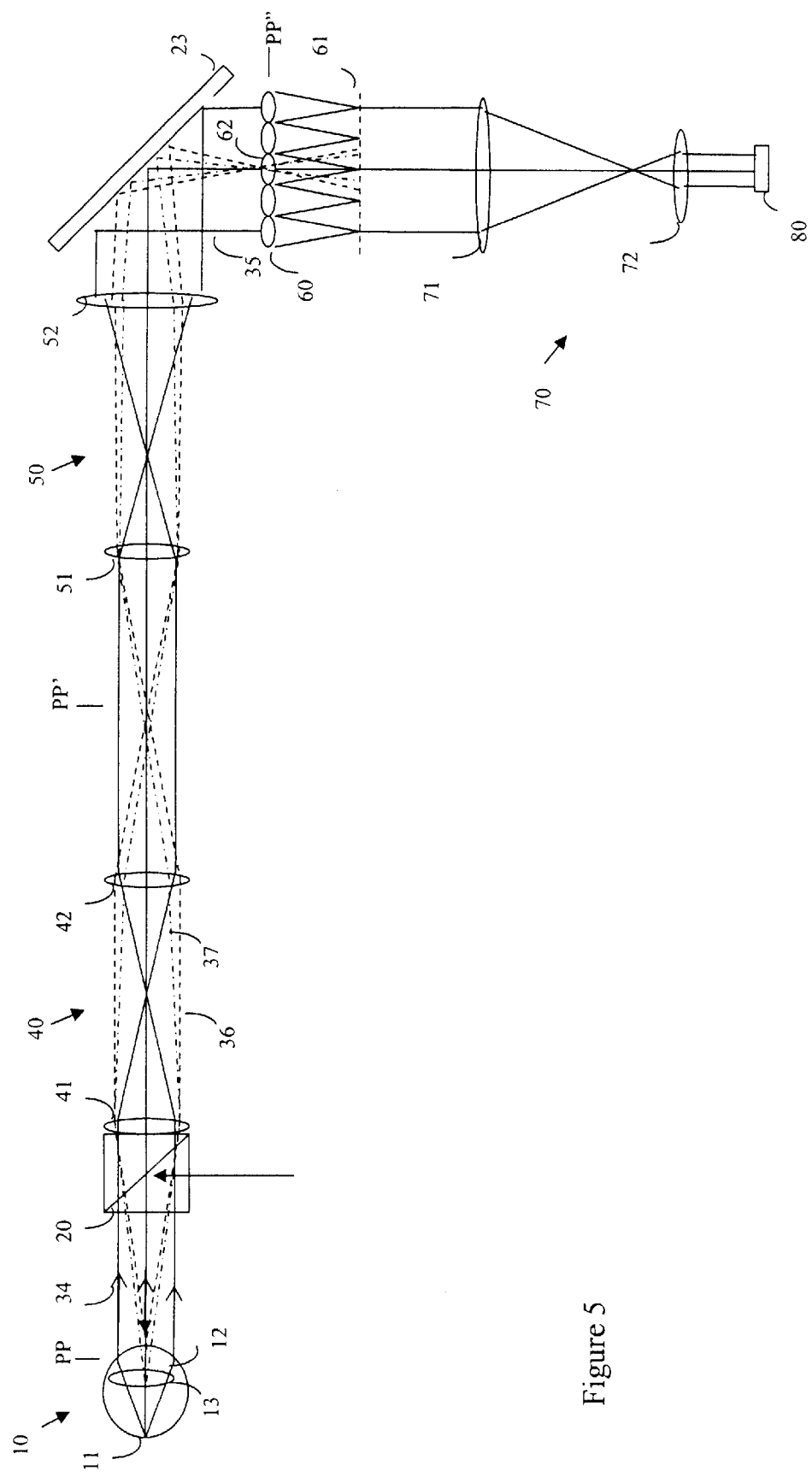
FIG. 5 is a schematic diagram of a portion of an aberration measurement instrument that illustrates how radiation reflected from a cornea and radiation scattered by intraocular elements can contaminate a Hartmann-Shack image.

IV. Blocking Radiation Reflected from the Cornea and Radiation Scattered by Intra-Ocular Elements FIG. 5 is a schematic diagram of a portion of an aberration measurement instrument that illustrates how radiation reflected from a cornea (radiation 36) and radiation scattered by intra-ocular elements of eye 10 (radiation 37) can contaminate Hartmann-Shack spot pattern 61. Radiation reflected from a cornea and radiation scattered by intra-ocular elements can usually be much stronger than radiation scattered by the retina 11. Although much radiation reflected by the cornea can be rejected by use of polarizing beam splitter 20 to embody coupler 1000 of FIG. 1, residual corneal reflection 36 remains troublesome for precise wavefront measurement. In addition, radiation scattered by intra-ocular elements (for example, crystalline lens 13 and the cornea), is depolarized in a manner that is similar to depolarization produced by scattering by retina 11. Thus, radiation scattered by intra-ocular elements cannot be removed by polarized beam splitter 20. Finally, since radiation 36 that is reflected by the cornea and radiation 37 that is scattered by intra-ocular elements originate from the path of narrow probe beam 33, they are focused into small spots near first conjugate plane PP' or second conjugate plane PP" (for example, at lenslet 62 of lenslet array 60) of exit pupil plane PP. As a result, such radiation decreases the accuracy of wavefront measurements.

Figure 6:
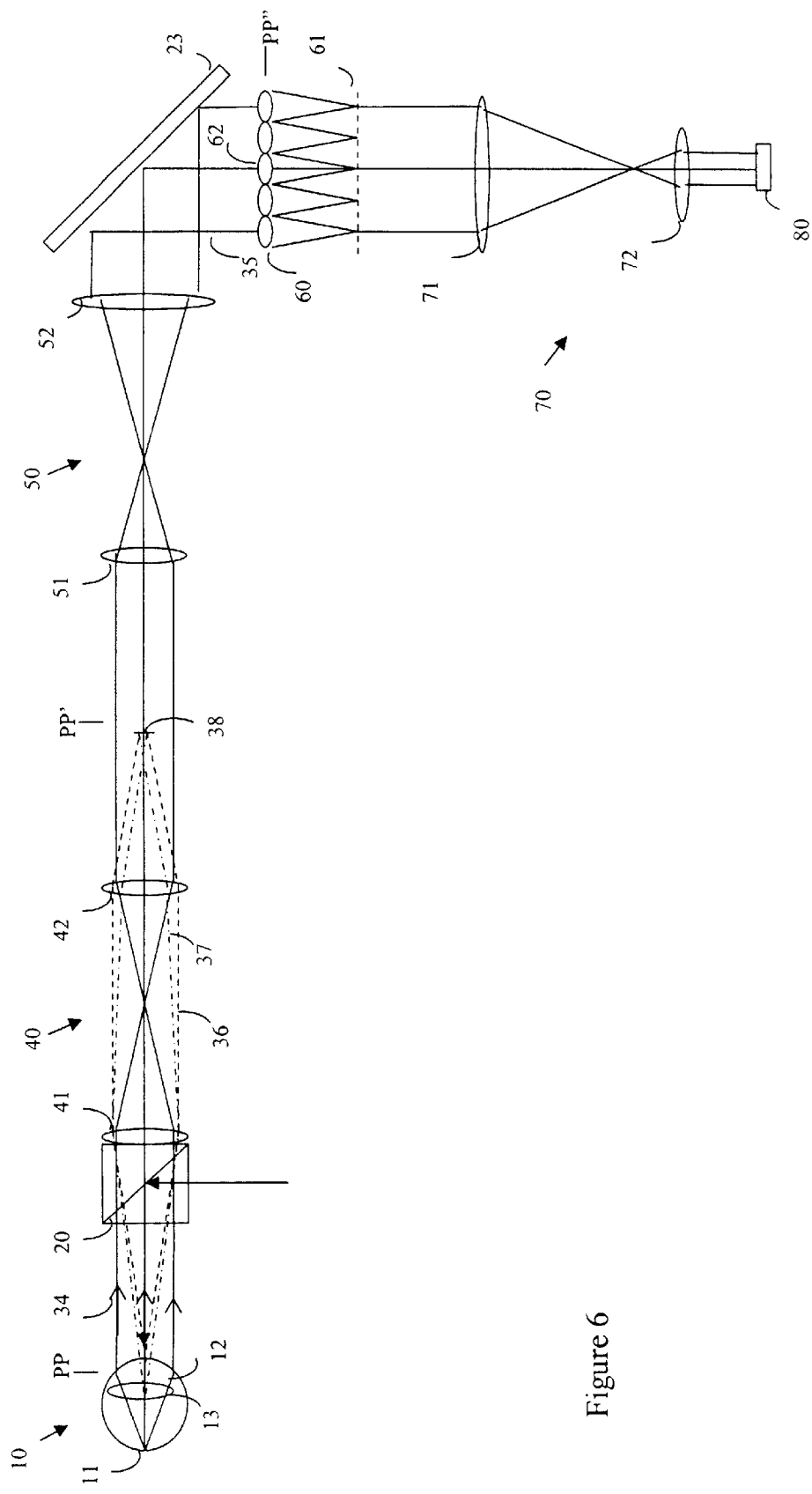
FIG. 6 is a schematic diagram showing an obscuration member that is used to fabricate an aberration measurement instrument in accordance with one or more embodiments of the present invention.

FIG. 6 is a schematic diagram showing obscuration member 38 that is used to fabricate an aberration measurement instrument in accordance with one or more embodiments of the present invention, which obscuration member blocks radiation 36 reflected from a cornea and radiation 37 scattered from intra-ocular elements of eye 10. As shown in FIG. 6, in one embodiment, obscuration member 38 is inserted into an optical path of emerging beam 34, and is located near a conjugate plane of exit pupil plane PP (for example, first conjugate plane PP' of exit pupil plane PP). For example, to block radiation 36 and radiation 37, obscuration member 38 can be located between focal images of radiation 36 and radiation 37.

In accordance with one embodiment of the present invention, lenslet array 60 is aligned to have one lenslet thereof (a predetermined lenslet) positioned to intercept focal images of radiation 36 and radiation 37 (i.e., as can be understood by referring to FIGS. 5 and 6, lenslet array 60 is positioned and aligned such that one lenslet, for example, lenslet 62, is overlapped substantially with an image of radiation reflected from the cornea and radiation scattered by intra-ocular elements). This is possible whenever the spot size of probe beam 33 is such that its image spot size on lenslet array 60 is smaller than a sub-aperture of a lenslet of lenslet array 60. In this case, obscuration member 38 is dimensioned and aligned laterally such that its image or shadow is substantially overlapped with the predetermined lenslet, for example, lenslet 62. In one example of such an embodiment, obscuration member 38 is formed by printing, for example, a black spot on a transparency, for example, a piece of transparent plastic, and by affixing the transparency to an x-y-z adjustable mount (not shown). Such an adjustable mount may be fabricated in accordance with any one of a number of methods that are well known to those of ordinary skill in the art. In one embodiment, the spot size of probe beam 33 is about 250 microns on the cornea, and its image spot size is about 250 microns at first conjugate plane PP', and is about 350 microns at second conjugate plane PP". In addition, the sub-aperture size of lenslet array 60 is about 600 microns, and obscuration member 38 has a dimension of approximately 430 microns across a black spot.

Figure 7:
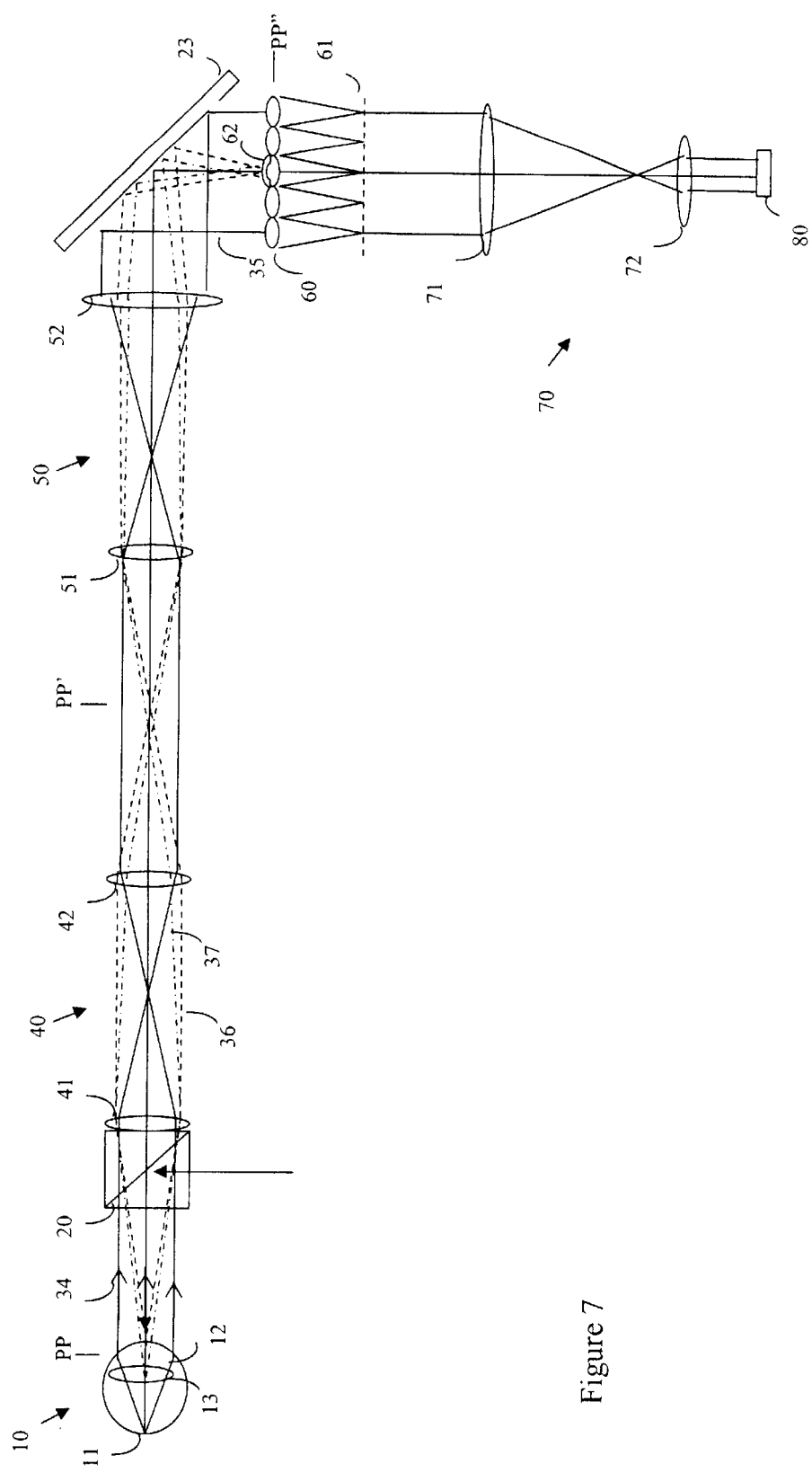
FIG. 7 is a schematic diagram showing an aberration measurement instrument that is fabricated in accordance with one or more embodiments of the present invention wherein a lenslet of a Hartmann-Shack sensor is treated to block radiation.

FIG. 7 is a schematic diagram showing an aberration measurement instrument that is fabricated in accordance with one or more embodiments of the present invention wherein a lenslet of a Hartmann-Shack sensor is treated to block radiation reflected from a cornea and radiation scattered by intra-ocular elements. In accordance with this embodiment, lenslet array 60 is aligned to have one lenslet thereof, for example, lenslet 62, positioned to intercept focal images of radiation 36 and radiation 37 (i.e., lenslet array 60 is positioned and aligned such that lenslet 62, is overlapped substantially with an image of radiation reflected from the cornea and radiation scattered by intra-ocular elements). As shown in FIG. 7, lenslet 62 is disposed at a position that is substantially conjugate to a position where radiation reflected by the cornea, and radiation scattered by the intra-ocular elements, are focused near first conjugate plane PP'. Then, lenslet 62, is made opaque (for example, it is blackened) to serve as an obscuration member. Although this embodiment has been described as making a lenslet opaque, embodiments of the present invention include further embodiments wherein an obscuration member replaces a lenslet of a lenslet array.

Note, although blocking of radiation reflected from the cornea and radiation scattered from intra-ocular elements was described in the context of FIGS. 5–7 that show instruments comprising two optical relay modules (i.e., first optical module 40 and second optical module 50), embodiments of the present invention are not limited thereto. In particular, other embodiments can be formed wherein a single optical relay module 1010 is utilized (see FIG. 1). Such other embodiments can be fabricated wherein a lenslet array is placed at a conjugate plane of radiation scattered from intra-ocular elements not originating from a corneal plane (a "new plane"). In such a case, a lenslet array element may be made opaque as described above. The placement of the lenslet array at the new plane is chosen to suppress interfering signals with a minimal loss of valid measurement data. Then, wavefront measurement data obtained using the new plane can be processed to provide wavefront measurements at a plane conjugate to exit pupil plane PP (or at any other reference plane of interest) in accordance with numerical or analytical methods that are well known to those or ordinary skill in the art to determine free-space propagation of this wavefront.

V. Reducing Haze Produced by Multiply Scattered Radiation

Figure 8:
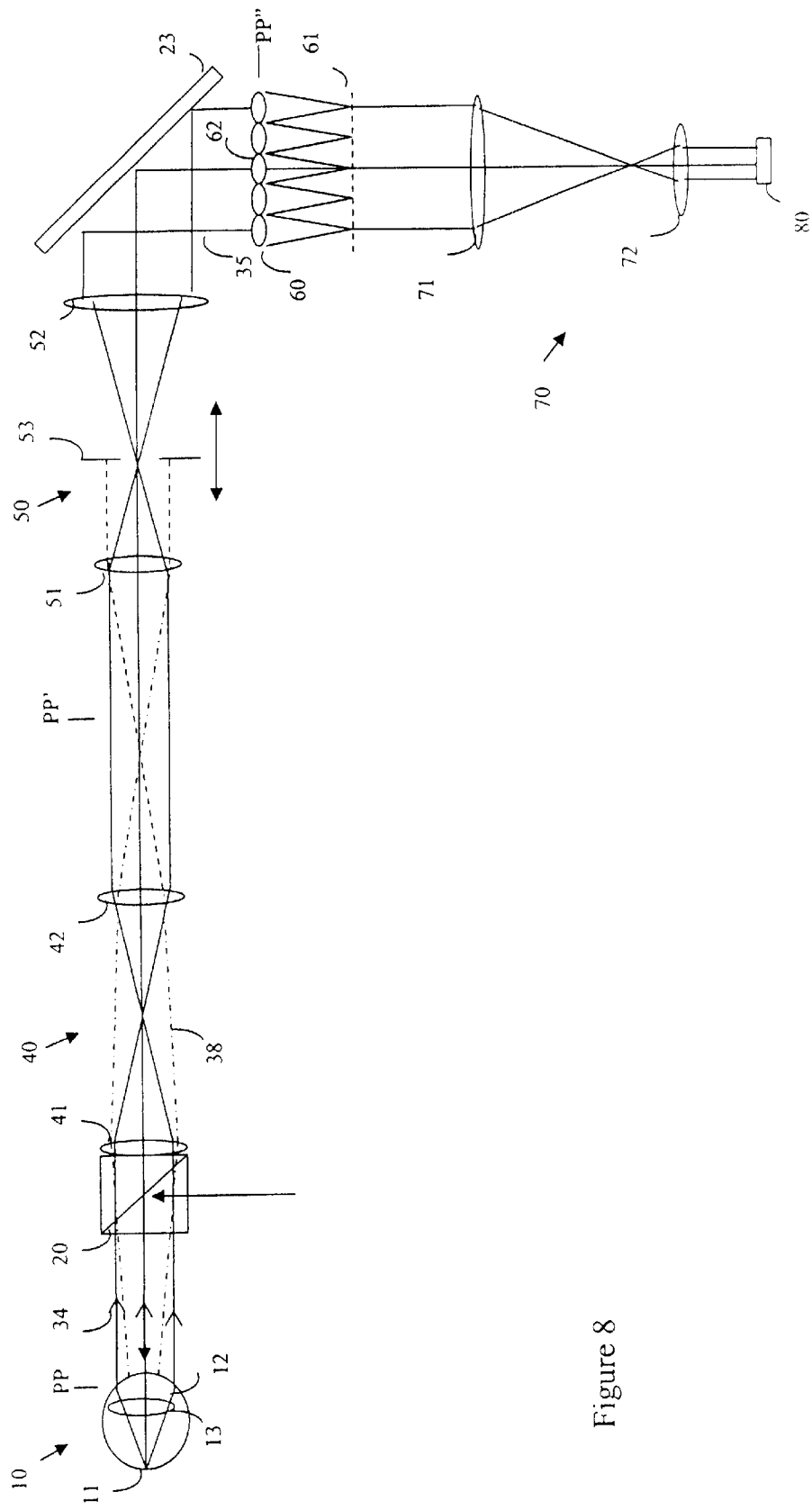
FIG. 8 is a schematic diagram showing a dynamic haze stop that is used to fabricate an aberration measurement instrument in accordance with one or more embodiments of the present invention.

FIG. 8 is a schematic diagram showing dynamic haze stop 53 that is used to fabricate an aberration measurement instrument in accordance with one or more embodiments of the present invention, which dynamic haze stop 53 reduces haze produced by multiply scattering radiation. Multiply scattered radiation 38 is trace light that originates from the interior of eye 10, and emerges from pupil 12 in all directions. Multiply scattered radiation 38 may produce a hazy background in a Hartmann-Shack image, and thereby affect the accuracy of wavefront measurement.

In accordance with this embodiment of the present invention, dynamic haze stop 53 is placed near a plane conjugate to retina 11, where emerging beam 34 is focused and is spatially separated from most of the trace light. In accordance with one such embodiment, dynamic haze stop 53 is translated by a translation stage driven by a motor (not shown) in response to signals from, for example, analyzer 40 of FIG. 1, which translation stage and motor can be fabricated in accordance with any one of a number of methods that are well known to those of ordinary skill in the art.

In operation, dynamic haze stop 53 may be initially parked at a nominal position or flipped away from an optical path of the instrument. The aberration measurement instrument then takes an initial wavefront measurement to estimate defocusing errors and astigmatism error of eye 10. Then, analyzer 1040 of FIG. 1 uses the measured wavefront data to calculate an approximate position of a plane conjugate to retina 11 in accordance with any one of a number of methods that are well known to those of ordinary skill in the art. Finally, analyzer 1040 sends a signal to the translation stage to cause it to move dynamic haze stop 53 to approximate position of the plane conjugate to retina 11. In accordance with one embodiment, the size of dynamic haze stop 53 is chosen to be large enough to allow beam 34 to pass without substantial loss, and to be small enough to remove a substantial amount of multiply scattered radiation light 38. In one embodiment dynamic haze stop 53 has an aperture having a dimension across the opening in a range from about 3 to about 5 mm.

Those skilled in the art will recognize that the foregoing description has been presented for the sake of illustration and description only. As such, it is not intended to be exhaustive or to limit the invention to the precise form disclosed. For example, embodiments of the present invention may include combinations of one or more of the embodiments described above. Further, in accordance with one or more embodiments of the present invention, measurement data produced by analyzer 1040 shown in FIG. 1 may be presented and/or saved in a digital format. Further, such data can be used, for example and without limitation, for performing customized refractive surgery, for making customized contact lenses, or for designing customized intra-ocular lenses.

What is claimed is:

1. An aberration measurement instrument for determining aberrations of an eye that comprises:
   a probe beam projector that outputs a probe beam of radiation;
   a coupler that couples the probe beam of radiation into the eye;
   relay optics that relays a wavefront of an emerging beam at a pupil plane to a plane;
   a Hartmann-Shack sensor disposed at the plane that produces a Hartmann-Shack spot pattern; and
   a detector responsive to the Hartmann-Shack spot pattern;
   wherein the probe beam projector includes an oscillating lens.

2. The aberration measurement instrument of claim 1 wherein the oscillating lens is driven by a voice coil.

3. The aberration measurement instrument of claim 2 wherein the voice coil is driven at an oscillating frequency of approximately 20–100 Hz.

4. The aberration measurement instrument of claim 1 wherein the probe beam projector includes a laser source of radiation.

5. The aberration measurement instrument of claim 1 wherein the probe beam projector includes a superluminescence diode source of radiation.

6. The aberration measurement instrument of claim 1 wherein the relay optics has magnification greater than 1.

7. The aberration measurement instrument of claim 6 wherein the detector includes a second relay optics having magnification <1.

8. An aberration measurement instrument for determining aberrations of an eye that comprises:
   a probe beam projector that outputs a probe beam of radiation;
   a coupler that couples the probe beam of radiation into the eye;
   relay optics that relays a wavefront of an emerging beam at a pupil plane to a plane;
   a Hartmann-Shack sensor disposed at the plane that produces a Hartmann-Shack spot pattern; and
   a detector responsive to the Hartmann-Shack spot pattern;
   wherein the aberration measurement instrument further includes an optometer module coupled to the eye.

9. The aberration measurement instrument of claim 8 wherein the optometer module comprises a movable lens that compensates defocusing error of the eye.

10. The aberration measurement instrument of claim 8 wherein the optometer module comprises a pair of Stokes' lenses that compensate astigmatism of the eye.

11. The aberration measurement instrument of claim 8 wherein the relay optics has magnification greater than 1.

12. An aberration measurement instrument for determining aberrations of an eye that comprises:
    a probe beam projector that outputs a probe beam of radiation;
    a coupler that couples the probe beam of radiation into the eye;
    relay optics that relays a wavefront of an emerging beam at a pupil plane to a plane;
    a Hartmann-Shack sensor disposed at the plane that produces a Hartmann-Shack spot pattern; and
    a detector responsive to the Hartmann-Shack spot pattern;
    wherein the aberration measurement instrument further includes an obscuration member located at or near a plane conjugate to the pupil plane.

13. The aberration measurement instrument of claim 12 wherein the obscuration member is printed on a transparency.

14. The aberration measurement instrument of claim 12 wherein the Hartmann-Shack sensor comprises a lenslet array and the obscuration member comprises an opaque area of the lenslet array.

15. The aberration measurement instrument of claim 14 wherein the opaque area comprises an opaque lenslet.

16. The aberration measurement instrument of claim 12 wherein the relay optics has magnification greater than 1.

17. An aberration measurement instrument for determining aberrations of an eye that comprises:
   a probe beam projector that outputs a probe beam of radiation;
   a coupler that couples the probe beam of radiation into the eye;
   relay optics that relays a wavefront of an emerging beam at a pupil plane to a plane;
   a Hartmann-Shack sensor disposed at the plane that produces a Hartmann-Shack spot pattern; and
   a detector responsive to the Hartmann-Shack spot pattern;
   wherein the Hartmann-Shack sensor comprises a lenslet array located so that a predetermined area thereof is overlapped substantially with an image of radiation reflected from a cornea of the eye and radiation scattered by intra-ocular elements of the eye; and aberration measurement instrument further includes an obscuration member.

18. The aberration measurement instrument of claim 17 wherein the obscuration member is located so that its image is substantially overlapped with the predetermined area.

19. The aberration measurement instrument of claim 17 wherein the obscuration member blocks radiation at the position of the predetermined area.

20. The aberration measurement instrument of claim 17 wherein the relay optics has magnification greater than 1.

21. An aberration measurement instrument for determining aberrations of an eye that comprises:
   a probe beam projector that outputs a probe beam of radiation;
   a coupler that couples the probe beam of radiation into the eye;
   relay optics that relays a wavefront of an emerging beam at a pupil plane to a plane;
   a Hartmann-Shack sensor disposed at the plane that produces a Hartmann-Shack spot pattern; and
   a detector responsive to the Hartmann-Shack spot pattern;
   wherein the relay optics includes a dynamic haze stop located at approximately a conjugate plane of a retina.

22. The aberration measurement instrument of claim 21 wherein the relay optics has magnification greater than 1.

23. A method of determining aberrations of an eye that includes steps of:
   projecting light from an optometer into the eye;
   projecting a probe beam of radiation into the eye;
   relaying a wavefront of an emerging beam at a pupil plane to a Hartmann-Shack sensor;
   detecting a Hartmann-Shack spot pattern; and
   analyzing the Hartmann-Shack spot pattern to determine the optical aberrations of the eye, including defocusing errors and astigmatism; and
   adjusting the optometer in response to the defocusing errors and astigmatism.

24. The method of claim 23 which comprises performing the steps of determining and adjusting until a measured defocusing error and astimagtism are stabilized within a predetermined range.

25. A method of determining aberrations of an eye that includes steps of:
   projecting a probe beam of radiation into the eye;
   relaying a wavefront of an emerging beam at a pupil plane to a Hartmann-Shack sensor;
   detecting a Hartmann-Shack spot pattern; and
   analyzing the Hartmann-Shack spot pattern to determine the optical aberrations of the eye, including defocusing errors and astigmatism;
   determining an approximate position of a plane conjugate to a retina of the eye; and
   moving a haze stop to the position.

* * * * *